United States Patent [19]

Inaba et al.

[11] 4,202,895
[45] May 13, 1980

[54] 1-POLYHALOALKYL-2(1H)-QUINAZOLI-NONE DERIVATIVES

[75] Inventors: Shigeho Inaba, Takarazuka; Michihiro Yamamoto, Toyonaka; Kikuo Ishizumi, Ikeda; Kazuo Mori, Kobe; Hisao Yamamoto, Nishinomiya, all of Japan

[73] Assignee: Sumitomo Chemical Company, Limited, Osaka, Japan

[21] Appl. No.: 479,464

[22] Filed: Jun. 14, 1974

Related U.S. Application Data

[63] Continuation-in-part of Ser. No. 153,031, Jun. 4, 1971, abandoned.

[51] Int. Cl.² .................. A61K 31/505; C07D 239/82
[52] U.S. Cl. ...................................... 424/250; 544/286
[58] Field of Search ............... 260/251 QB; 424/250; 544/286

[56] References Cited

U.S. PATENT DOCUMENTS

| | | | |
|---|---|---|---|
| 3,549,635 | 12/1970 | Ott | 260/251 |
| 3,551,427 | 12/1970 | Ott | 260/251 |
| 3,712,892 | 1/1973 | Inaba et al. | 260/251 QB |
| 3,812,118 | 5/1974 | Yamamoto et al. | 260/247.1 |
| 3,829,420 | 8/1974 | Inaba et al. | 260/251 QB |
| 3,859,237 | 1/1975 | Inaba et al. | 260/251 QB |
| 3,910,911 | 10/1975 | Ishizumi et al. | 260/251 QB |
| 3,923,710 | 12/1975 | Ishizumi et al. | 260/251 QB |
| 3,925,382 | 12/1975 | Ishizumi et al. | 260/251 QB |
| 3,926,993 | 12/1975 | Ishizumi et al. | 260/251 QB |
| 3,953,446 | 4/1976 | Ishizumi et al. | 260/251 QB |

FOREIGN PATENT DOCUMENTS 1520743  4/1968 France .

OTHER PUBLICATIONS

Yamamoto et al. (II)—C.A. 78, 72196b (1973).
Yamamoto et al. (III)—C.A. 79, 149319z (1973).

Primary Examiner—Donald G. Daus
Assistant Examiner—James H. Turnipseed
Attorney, Agent, or Firm—Stevens, Davis, Miller & Mosher

[57] ABSTRACT

1-Polyhaloalkyl-2(1H)-quinazoline derivatives of the formula,

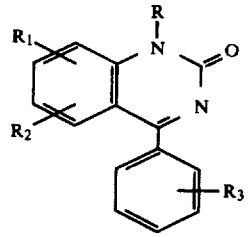

wherein R is polyhaloalkyl having $C_2$–$C_4$ alkyl; and $R_1$, $R_2$ and $R_3$ are individually hydrogen, $C_1$–$C_4$ alkyl, $C_1$–$C_4$ alkoxy, nitro, trifluoromethyl or halogen, have excellent anti-inflammatory and analgesic activities with very low toxicity. These quinazolinone derivatives can be prepared, for example, by reacting a trihalogenoacetamidobenzophenone derivative with ammonia.

14 Claims, No Drawings

1-POLYHALOALKYL-2(1H)-QUINAZOLINONE DERIVATIVES

CROSS REFERENCE TO THE RELATED APPLICATION

This application is a continuation-in-part of application Ser. No. 153,031 filed June 14, 1971, now abandoned.

This invention relates to novel quinazolinone derivatives and a process for the production of the same.

More particularly, this invention pertains to novel quinazolinone derivatives represented by the formula,

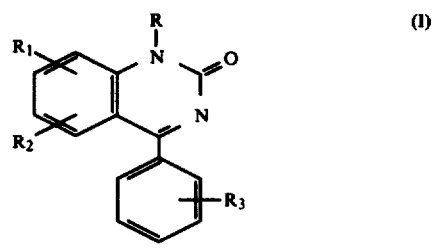

wherein R is polyhaloalkyl having $C_2$–$C_4$ alkyl; and $R_1$, $R_2$ and $R_3$ are individually hydrogen, $C_1$–$C_4$ alkyl, $C_1$–$C_4$ alkoxy, nitro, trifluoromethyl or halogen; and pharmaceutical use of the same.

In the compounds represented by the formula (I), the term "polyhaloalkyl" refers to $C_2$–$C_4$ alkyl groups substituted with two or more halogen atoms and preferably includes such moieties as 2,2-difluoroethyl, 2,2,2-trifluoroethyl, 2,2,2-trichloroethyl, 2-bromo-2,2-difluoroethyl, 2-chloro-2,2-difluoroethyl, trifluoromethyl, 2,2,3,3-tetrafluoropropyl, 2,2,3,3,3-pentafluoropropyl and 2,2,3,3,4,4,4-heptafluorobutyl and the like. The term "alkyl" represents and is intended to cover both straight and branched chain aliphatic hydrocarbon radicals, and $C_1$–$C_4$ alkyl includes, for example, methyl, ethyl, n-propyl, n-butyl and iso-propyl; $C_1$–$C_4$ alkoxy includes, for example, methoxy, ethoxy, n-propoxy, n-butoxy and isopropoxy. The term "halogen" includes all halogens, and fluorine, chlorine or bromine is preferable.

The quinazolinone derivatives of the formula (I) have excellent anti-inflammatory and analgesic activities and possess very low toxicity.

Preferred compounds falling within the formula (I) have polyfluoroalkyl having $C_2$–$C_3$ alkyl as R, and more preferred compounds have polyfluoroethyl as R.

Illustratively, 1-(2,2,2-trifluoroethyl)-4-phenyl-6-chloro-2(1H)-quinazolinone and 1-(2,2,2-trifluoroethyl)-4-phenyl-6-methoxy-2(1H)-quinazolinone show remarkable inhibitory action for carrageenin-induced edema in rats and they are also very effective on adjuvant-induced arthritis in rats, while no toxic symptoms are observed and occult bleeding in feces is negative after oral administration to the rat of 1,000 mg/kg of body weight. The anti-inflammatory activity of the compound is more potent than that of 1,2-diphenyl-3,5-dioxo-4-n-butylpyrazolidine (phenylbutazone), and the acute, subacute and chronic toxicities are much lower than those of phenylbutazone.

The compounds of the present invention can be administered orally or parenterally in therapeutic dosage forms with dosage adjusted to individual needs, that is, in solid or liquid dosage forms such as tablets, dragees, capsules, suspensions, solutions, elixirs and the like.

Accordingly, an object of the present invention is to provide novel and useful quinazolinone derivatives which have excellent pharmacological properties.

Another object is to provide processes for producing commercially such valuable compounds.

These and further objects will be apparent from the following description.

The novel quinazolinones of the aforesaid formula (I) can be prepared using a variety of known methods as described below.

One method for synthesis of the compounds of the formula (I), comprises reacting a compound of the formula,

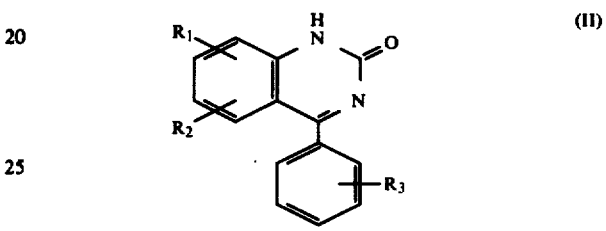

wherein $R_1$, $R_2$ and $R_3$ are as defined above, with a reactive ester of a compound of the formula,

R—OH  (III)

wherein R is as defined above. The reaction may be carried out by reacting a compound of the formula (II) with a reactive ester of a compound of the formula (III) in the presence of a condensing agent, or alternatively by treating the compound of the formula (II) with a condensing agent in a solvent to form a metal salt and then reacting the metal salt with the reactive ester of the compound of the formula (III).

As the reactive ester of the compound of the formula (III), there may be preferably used a hydrohalic acid ester such as chloride, bromide or iodide, or a sulfonic acid ester such as methanesulfonic acid ester, trichloromethanesulfonic acid ester or p-toluenesulfonic acid ester.

Suitable condensing agents include, for example, sodium hydride, potassium hydride, sodium amide, potassium amide, butyllithium, phenyllithium, sodium methylate, potassium methylate, sodium ethylate and potassium ethylate.

Suitable solvents include, for example, aromatic hydrocarbons such as benzene, toluene, xylene monochlorobenzene; amides such as dimethylacetamide, diethylacetamide, dimethylformamide; ethers such as diethylether, tetrahydrofuran, dioxane; and dimethyl sulfoxide. The choice of the solvent may depend on the reactive ester and the condensing agent to be employed.

The reaction is generally effected at a temperature in the range between room temperature and the boiling point of the solvent used.

The reaction is generally accompanied by formation of the quinazoline derivatives of the formula,

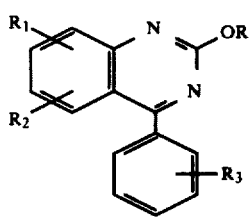

wherein $R_1$, $R_2$, $R_3$ and R are as defined above.

The separation of the desired compound of the formula (I) and the compound of the formula (IV) may be effected using conventional techniques, for example, by chromatography or fractional crystallization.

Another method comprises reacting a compound of the formula,

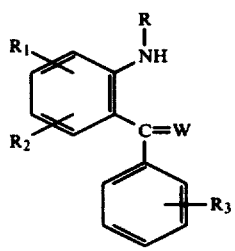

wherein R, $R_1$, $R_2$ and $R_3$ are as defined above, and W is oxygen or imino, with a carbamic acid ester, a carbamic acid halide or urea.

The reaction may be carried out by reacting a compound of the formula (V) with a carbamic acid ester or a crabamic acid halide in the presence of a Lewis acid such as zinc chloride, otherwise with urea in the presence of a solvent such as acetic acid.

Examples of carbamic acid esters include methyl carbamate, ethyl carbamate, isopropyl carbamate and benzyl carbamate. Examples of carbamic acid halides include carbamyl chloride.

The reaction is preferably carried out at a temperature of from about 100° C. to about 200° C.

A further method comprises reacting a compound of the formula,

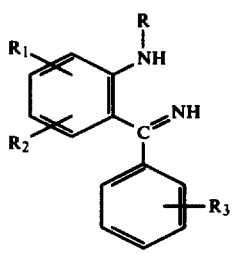

wherein R, $R_1$, $R_2$ and $R_3$ are as defined above, with a carbonic acid derivative of the formula,

wherein Y and Z are each chlorine, lower alkoxy, benzyloxy, lower alkylthio, trichloromethyl or 1-imidazolyl.

The reaction may be carried out in the presence or absence of an inert solvent and a basic condensing agent.

As the carbonic acid derivative of the formula (VI), there may be preferably used phosgene, methyl chlorocarbonate, ethyl chlorocarbonate, isopropyl chlorocarbonate, benzyl chlorocarbonate, ethyl chlorothiolformate, trichloroacetyl chloride, hexachloroacetone or 1,1'-carbonyldiimidazole.

Suitable solvents include, for example, benzene, toluene, xylene, chlorobenzene, pyridine, diethyl ether, isopropyl ether, tetrahydrofuran, dioxane, chloroform, dichloroethane, dimethylformamide and the like.

Suitable basic condensing agents include, for example, inorganic bases such as sodium hydroxide, potassium hydroxide, sodium carbonate or potassium carbonate, and tertiary amines such as triethylamine, N,N-dimethyl aniline or pyridine.

The reaction temperature may vary from about room temperature to the boiling point of the solvent used, depending on the carbonic acid derivative employed.

A still further method for preparing the compounds of the formula (I) comprises reacting a compound of the formula,

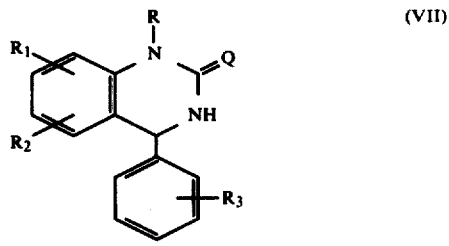

wherein R, $R_1$, $R_2$ and $R_3$ are as defined above, and Q is oxygen or sulfur, with an oxidizing agent.

Suitable oxidizing agents include, for example, potassium permanganate, sodium permanganate, manganese dioxide, chromium trioxide, magnesium dioxide and sodium metaperiodate.

The reaction may be carried out in the presence of an inert solvent or solvent mixture.

Examples of the solvent include benzene, toluene, ether, tetrahydrofuran, dioxane, chloroform, carbon tetrachloride, acetone, ethanol, isopropanol, acetic acid, dimethylformamide, dimethyl sulfoxide and water and a mixture thereof.

The reaction is generally effected at a temperature in the range between about room temperature and the boiling point of the solvent employed.

The starting compounds of the formula (VII) can be, for example, obtained by reacting a compound of the formula

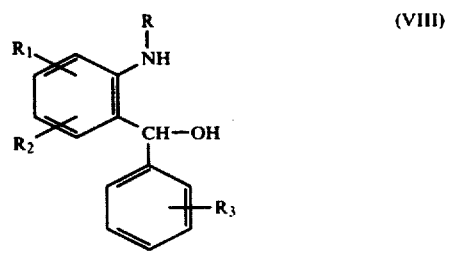

wherein R, $R_1$, $R_2$ and $R_3$ are as defined above, with a carbamic acid ester or carbamic acid halide, urea or thiocyanic acid or a salt thereof. The reaction may be effected by heating a compound of the formula (VIII) with a carbamic acid ester (e.g. methyl carbamate, ethyl carbamate or benzyl carbamate) or a carbamic acid halide (e.g. carbamyl chloride) in the presence of a Lewis acid such as zinc chloride, otherwise with thiocyanic acid or a salt thereof (e.g. sodium thiocyanate or ammonium thiocyanate) or urea in the presence of an acidic solvent, such as acetic acid.

The other method for preparing the compounds of the formula (I), comprises reacting a compound of the formula,

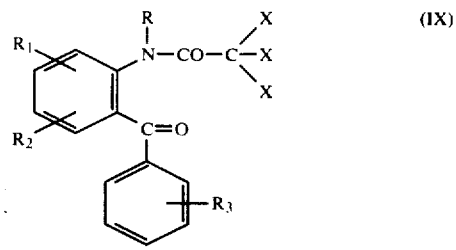
(IX)

wherein R, $R_1$, $R_2$ and $R_3$ are as defined above, and X is halogen, with ammonia.

The reaction may be carried out in the presence of a solvent or solvent mixture. Examples of the solvent include methanol, ethanol, isopropanol, tertiarybutanol, 2-ethoxyethanol, water, tetrahydrofuran, dioxane, acetone, pyridine, benzene, toluene, dimethylsulfoxide and dimethylformamide and mixture thereof. Ammonia is added to the reaction mixture as gaseous ammonia, alcoholic ammonia (e.g. methanolic or ethanolic ammonia), liquid ammonia or ammonium salt (e.g. ammonium acetate, ammonium formate, ammonium carbamate or ammonium succinate) which generates ammonia during the reaction. The reaction generally proceeds at room temperature, but the temperature may be higher or lower, if necessary, to effect the desired control of the reaction.

The starting compounds of the formula (IX) can be conveniently obtained by reacting a compound of the formula,

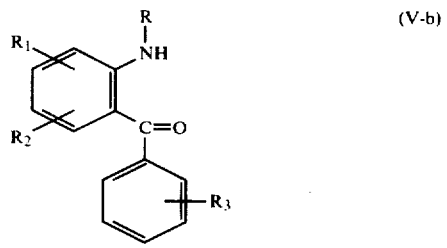
(V-b)

wherein R, $R_1$, $R_2$ and $R_3$ are as defined above, with a trihalogenoacetic acid, or a reactive derivative thereof, represented by the formula,

(X)

wherein X is as defined above. Examples of the reactive derivatives of the trihalogenoacetic acid include acid halides and acid anhydrides.

According to these processes, there are obtained, for example, the following quinazolinone derivatives:

1-(2,2,2-trifluoroethyl)-4-phenyl-2(1H)-quinazolinone
1-(2,2,2-trifluoroethyl)-4-phenyl-6-chloro-2(1H)-quinazolinone
1-(2,2,2-trifluoroethyl)-4-phenyl-6-bromo-2(1H)-quinazolinone
1-(2,2,2-trifluoroethyl)-4-phenyl-6-fluoro-2(1H)-quinazolinone
1-(2,2,2-trifluoroethyl)-4-phenyl-5-chloro-2(1H)-quinazolinone
1-(2,2,2-trifluoroethyl)-4-phenyl-7-chloro-2(1H)-quinazolinone
1-(2,2,2-trifluoroethyl)-4-phenyl-8-chloro-2(1H)-quinazolinone
1-(2,2,2-trifluoroethyl)-4-phenyl-6,8-dichloro-2(1H)-quinozolinone
1-(2,2,2-trifluoroethyl)-4-(o-fluorophenyl)-6-chloro-2(1H)-quinazolinone
1-(2,2,2-trifluoroethyl)-4-(p-methoxyphenyl)-6-chloro-2(1H)-quinazolinone
1-(2,2,2-trifluoroethyl)-4-(p-tolyl)-2(1H)-quinazolinone
1-(2,2,2-trifluoroethyl)-4-phenyl-6-methyl-2(1H)-quinazolinone
1-(2,2,2-trifluoroethyl)-4-phenyl-7-methyl-2(1H)-quinazolinone
1-(2,2,2-trifluoroethyl)-4-phenyl-6,7-dimethoxy-2(1H)-quinazolinone
1-(2,2,2-trifluoroethyl)-4-phenyl-6-methoxy-2(1H)-quinazolinone
1-(2,2,2-trifluoroethyl)-4-phenyl-7-methoxy-2(1H)-quinazolinone
1-(2,2,2-trifluoroethyl)-4-phenyl-6-nitro-2(1H)-quinazolinone
1-(2,2,2-trifluoroethyl)-4-phenyl-6-trifluoromethyl-2(1H)-quinazolinone
1-(2,2-difluoroethyl)-4-phenyl-6-chloro-2(1H)-quinazolinone
1-(2,2-difluoroethyl)-4-phenyl-6-methoxy-2(1H)-quinazolinone
1-(2,2-difluoroethyl)-4-phenyl-6-nitro-2(1H)-quinazolinone
1-(2,2,2-trichloroethyl)-4-phenyl-6-chloro-2(1H)-quinazolinone
1-(2,2,2-trichloroethyl)-4-phenyl-6-methoxy-2(1H)-quinazolinone
1-(2-chloro-2,2-difluoroethyl)-4-phenyl-6-chloro-2(1H)-quinazolinone
1-(2-bromo-2,2-difluoroethyl)-4-phenyl-6-chloro-2(1H)-quinazolinone
1-(3,3,3-trifluoropropyl)-4-phenyl-6-chloro-2(1H)-quinazolinone
1-(2,2,3,3-tetrafluoropropyl)-4-phenyl-6-chloro-2(1H)-quinazolinone
1-(2,2,3,3,3-pentafluoropropyl)-4-phenyl-6-chloro-2(1H)-quinazolinone
1-(2,2,3,3,3-pentafluoropropyl)-4-phenyl-6-methyl-2(1H)-quinazolinone
1-(2,2,3,3,3-pentafluoropropyl)-4-phenyl-6-methoxy-2(1H)-quinazolinone
1-(2,2,3,3,4,4,4-heptafluorobutyl)-4-phenyl-6-methoxy-2(1H)-quinazolinone This invention is further disclosed in the following Examples of more preferred embodiment thereof, which are represented for the purpose of illustration and it is not intended to limit the scope of the invention.

EXAMPLE 1

To a suspension of 5.13 g of 4-phenyl-6-chloro-2(1H)-quinazolinone in 60 ml of dimethylformamide was added 0.85 g 62% sodium hydride, and the resulting mixture was stirred at 100° C. for 30 minutes. Thereafter, 10.0 g of 2,2,2-trifluoroethyl iodide was added and the mixture was stirred at 140° C. for 8 hours. After cooling, the reaction mixture was poured into 300 ml of water and the resulting mixture was extracted with chloroform. The chloroform layer was washed with water, dried over anhydrous sodium sulfate and concentrated under reduced pressure. The oily residue was absorbed on a silica gel column, eluted with chloroform to obtain 3.5 g of 1-(2,2,2-trifluoroethyl)-4-phenyl-6-chloro-2(1H)-quinazolinone which was recrystallized from ethanol to give pale yellow leaflets melting at 185.0°–186.0° C., and 2.0 g of 2-(2,2,2-trifluoroethoxy)-4-phenyl-6-chloroquinazoline which was recrystallized from ethanol to give pale yellow needles melting at 113.0°–114.0° C.

EXAMPLE 2

To a suspension of 3.78 g of 4-phenyl-6-methoxy-2(1H)-quinazolinone in 100 ml of dimethylformamide was added 0.77 g of 52.9% sodium hydride, and the resulting mixture was stirred at 55° C. for 1 hour. Thereafter, 4.9 g of 2,2,2-trifluoroethyl bromide and 7.5 g of potassium iodide were added, and the mixture was stirred at 120° C. for 7 hours. After cooling, the reaction mixture was poured into 400 ml. of water and the resulting mixture was extracted with chloroform. The extract was washed with water, dried over anhydrous sodium sulfate and then concentrated under reduced pressure.

The residue was absorbed on a silica gel column, eluted with chloroform to obtain 2.0 g of 1-(2,2,2-trifluoroethyl)-4-phenyl-6-methoxy-2(1H)-quinazolinone which was recrystallized from ethanolisopropyl ether to give yellow needles melting at 157.0°–158.0° C., and 1.44 g of 2-(2,2,2-trifluoroethoxy)-4-phenyl-6-methoxyquinazoline which was recrystallized from ethanol to give colorless fine crystals melting at 109.5°–110.5° C.

EXAMPLE 3

Using a procedure similar to that described in Example 2, but replacing 4-phenyl-6-methoxy-2(1H)-quinazolinone with 4-(o-fluorophenyl)-6-chloro-2(1H)-quinazolinone, there were obtained 1-(2,2,2-trifluoroethyl)-4-(o-fluorophenyl)-6-chloro-2(1H)-quinazolinone, m.p. 194.5°–195.5° C., and 2-(2,2,2-trifluoroethoxy)-4-(o-fluorophenyl)-6-chloroquinazoline, m.p. 131.0°–132.0° C.

EXAMPLE 4

Using a procedure similar to that described in Example 2, but replacing 4-phenyl-6-methoxy-2(1H)-quinazolinone with 4-phenyl-6-trifluoromethyl-2(1H)-quinazolinone, there were obtained 1-(2,2,2-trifluoroethyl)-4-phenyl-6-trifluoromethyl-2(1H)-quinazolinone, m.p. 173.0°–174.0° C., and 2-(2,2,2-trifluoroethoxy)-4-phenyl-6-trifluoromethylquinazoline, m.p. 81.0°–82.0° C.

EXAMPLE 5

A mixture of 62.7 g of 2-(2,2,2-trifluoroethylamino)-5-chlorobenzophenone, 107 g of ethyl carbamate and 10 g of zinc chloride was heated at 190° C. (oil bath temperature) for 3 hours. After cooling, the reaction mixture was dissolved in chloroform and the insoluble material was filtered off. The chloroform solution was washed successively with dilute hydrochloric acid and water, and dried over anhydrous sodium sulfate. Then the solvent was removed under reduced pressure and the residual solid was washed 3 times with 100 ml of isopropyl ether and dried to give 49.5 g of 1-(2,2,2-trifluoroethyl)-4-phenyl-6-chloro-2(1H)-quinazolinone as a pale gray powder. Recrystallization from ethanol gave pale yellow needles, m.p. 186.5°–187.5° C.

EXAMPLE 6

Using a procedure similar to that described in Example 5, there were obtained the following compounds using appropriate starting materials:

1-(2,2,2-trifluoroethyl)-4-phenyl-2(1H)-quinazolinone, m.p. 181.5°–182.0° C.;

1-(2,2,2-trifluoroethyl)-4-phenyl-6-methoxy-2(1H)-quinazolinone, m.p. 157.0°–158.0° C.;

1-(2,2,2-trifluoroethyl)-4-phenyl-6-nitro-2(1H)-quinazolinone, m.p. 195.0°–196.0° C.;

1-(2,2,3,3,3-pentafluoropropyl)-4-phenyl-6-methyl-2(1H)-quinazolinone, m.p. 175.5°–176.5° C.

EXAMPLE 7

To a mixture of 3.13 g of 2-(2,2,2-trifluoroethylamino)-5-chlorobenzophenonimine, 12 ml. of triethylamine and 70 ml. of benzene was added dropwise at 5°–10° C. with cooling 70 ml. of a 10% phosgene solution in benzene. The mixture was stirred at room temperature overnight and then concentrated under reduced pressure to dryness. To the residue were added 100 ml. of a dilute aqueous sodium carbonate solution and 100 ml. of chloroform and the resulting mixture was stirred well. The organic layer was separated and the aqueous layer was further extracted with chloroform. The combined organic layers were washed with water, dried over anhydrous sodium sulfate and concentrated under reduced pressure. The residue was absorbed on a silica gel column, eluted with chloroform to give 1-(2,2,2-trifluoroethyl)-4-phenyl-6-chloro-2(1H)-quinazolinone, m.p. 184.0°–185.0° C.

EXAMPLE 8

To a mixture of 2.8 g of 2-(2,2,2-trifluoroethylamino)-benzophenonimine, 2 ml. of ethyl chlorocarbonate and 20 ml. of benzene was added dropwise 2.0 g of triethylamine, and the mixture was heated under reflux for 3 hours. After cooling, the reaction mixture was washed with water and dried over anhydrous sodium sulfate. Then, the solvent was removed under reduced pressure. The residue was absorbed on a silica gel column, eluted with chloroform to obtain 1-(2,2,2-trifluoroethyl)-4-phenyl-2(1H)-quinazolinone, which was recrystallized from ethanol to give colorless crystals, m.p. 181.5°–182.0° C.

EXAMPLE 9

To a solution of 45 g of 1-(2,2,2-trifluoroethyl)-4-phenyl-6-chloro-3,4-dihydro-2(1H)-quinazolinone in 450 ml. of acetic acid was added dropwise at room temperature a solution of 13.2 g of chromium trioxide in 13.2 ml. of water. The mixture was stirred at room temperature overnight and then poured into 2 l of water. The resultant precipitate was collected by filtration, washed successively with diluted ammonia water and water, and dried to give 1-(2,2,2-trifluoroethyl)-4-phenyl-6-chloro-2(1H)-quinazolinone quantitatively.

EXAMPLE 10

Using a procedure similar to that described in Example 9, there were obtained the following compounds employing appropriate starting materials:

1-(2,2,2-trifluoroethyl)-4-phenyl-6-methoxy-2(1H)-quinazolinone, m.p. 157.5°–158.0° C.;

1-(2,2,2-trifluoroethyl)-4-phenyl-6-nitro-2(1H)-quinazolinone, m.p. 208.0°–208.5° C.;

1-(2,2-difluoroethyl)-4-phenyl-6-nitro-2(1H)-quinazolinone, m.p. 197.0°–197.5° C.;

1-(2,2,2-trichloroethyl)-4-phenyl-6-methoxy-2(1H)-quinazolinone, m.p. 217° C. (decomp.).

EXAMPLE 11

To a solution of 1.5 g of 1-(2,2,2-trifluoroethyl)-4-phenyl-6-chloro-3,4-dihydro-2(1H)-quinazolinethione in 50 ml. of dioxane was added dropwise a solution of 3 g of potassium permangenate in 20 ml. of water. The mixture was stirred at room temperature for 2 hours and then a few drops of formic acid was added. The resultant brown precipitate was filtered off and washed with chloroform. The filtrate was concentrated under reduced pressure and the residue was dissolved in 30 ml. of chloroform. The chloroform solution was combined, washed successively with dilute sodium hydroxide solution and water, and dried over anhydrous sodium sulfate. The solvent was removed under reduced pressure. The residue was recrystallized from isopropyl alcohol to give 1 g of 1-(2,2,2-trifluoroethyl)-4-phenyl-6-chloro-2(1H)-quinazolinone, m.p. 184.0°–185.0° C.

EXAMPLE 12

To a solution of 2.8 g of 2-[N-(2,2,2-trifluoroethyl)-trichloroacetamido]-5-chlorobenzophenone in 50 ml. of ethanol was added 4.6 g of ammonium acetate. The mixture was stirred and heated under reflux for 10 hours. Then the solvent was removed under reduced pressure. The residue was triturated with ether, filtered, washed with water and dried to give 1-(2,2,2-trifluoroethyl)-4-phenyl-6-chloro-2(1H)-quinazolinone. Recrystallization from ethanol gave pale yellow crystals, m.p. 185.0°–186° C.

EXAMPLE 13

Using a procedure similar to that described in Example 12 there were produced the following compounds:

1-(2,2,2-trifluoroethyl)-4-phenyl-2(1H)-quinazolinone, m.p. 181.5°–182.0° C.;

1-(2,2,2-trifluoroethyl)-4-phenyl)-6-methoxy-2(1H)-quinazolinone, m.p. 157.0°–158.0° C.;

1-(2,2,2-trifluoroethyl)-4-(o-fluorophenyl)-6-chloro-2(1H)-quinazolinone, m.p. 194.5°–195.5° C.;

1-(2,2,3,3,3-pentafluoropropyl)-4-phenyl-6-methyl-2(1H)-quinazolinone, m.p. 175.0°–176.0° C.

EXAMPLE 14

A mixture of 3.24 g of 2-(2,2,2-trifluoroethylamino)-5-nitrobenzophenone and 15 ml. of trichloroacetyl chloride was heated at 100° C. (bath temperature) for 5 hours. The volatiles were removed under reduced pressure. The residue was chromatographed on silica gel using benzene as an eluent to give 2-[N-(2,2,2-trifluoroethyl)trichloroacetamido]-5-nitrobenzophenone as an yellow oil.

To a solution of the above obtained compound in 50 ml. of tertiary-butanol was added 4 g of ammonium acetate. The resultant mixture was stirred under reflux for 8 hours. Then the solvent was removed under reduced pressure. To the residue was added water and chloroform. The chloroform layer was separated and the water layer was further extracted with chloroform. The combined extracts were washed successively with dilute ammonia water and water, and dried over anhydrous sodium sulfate. The solvent was removed under reduced pressure. The residue was chromatographed on silica gel using chloroform as an eluent to give 1-(2,2,2-trifluoroethyl)-4-phenyl-6-nitro-2(1H)-quinazolinone, m.p. 195.0°–196.0° C.

EXAMPLE 15

Using a procedure similar to that described in Example 13, there was produced the following compound:

1-(2,2,2-trifluoroethyl)-4-phenyl-6-trifluoromethyl-2(1H)-quinazolinone, m.p. 173.0°–174.0° C.

What is claimed:

1. A quinazolinone of the formula

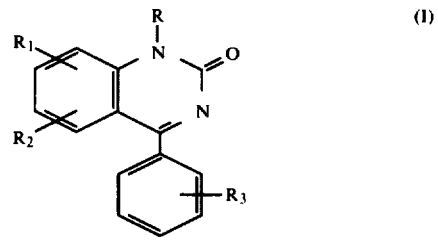

wherein R is a polyhaloalkyl having $C_2$–$C_3$ alkyl with at least two fluorine atoms; and $R_1$, $R_2$ and $R_3$ are individually hydrogen, $C_1$–$C_4$ alkyl, $C_1$–$C_4$ alkoxy, nitro, trifluoromethyl or halogen.

2. The quinazolinone according to claim 1 wherein R is a polyfluoroalkyl having $C_2$–$C_3$ alkyl.

3. The quinazolinone according to claim 2 wherein R is polyfluoroethyl.

4. The quinazolinone according to claim 3 wherein R is trifluoroethyl.

5. The compound according to claim 4 which is 1-(2,2,2-trifluoroethyl)-4-phenyl-2(1H)-quinazolinone.

6. The compound according to claim 4 which is 1-(2,2,2-trifluoroethyl)-4-phenyl-6-chloro-2(1H)-quinazolinone.

7. The compound according to claim 4 which is 1-(2,2,2-trifluoroethyl)-4-phenyl-6-bromo-2(1H)-quinazolinone.

8. The compound according to claim 4 which is 1-(2,2,2-trifluoroethyl)-4-phenyl-6,8-dichloro-2(1H)-quinazolinone.

9. The compound according to claim 4 which is 1-(2,2,2-trifluoroethyl)-4-(o-fluorophenyl)-6-chloro-2(1H)-quinazolinone.

10. The compound according to claim 4 which is 1-(2,2,2-trifluoroethyl)-4-phenyl-6-methyl-2(1H)-quinazolinone.

11. The compound according to claim 4 which is 1-(2,2,2-trifluoroethyl)-4-phenyl-6-methoxy-2(1H)-quinazolinone.

12. The compound according to claim 4 which is 1-(2,2,2-trifluoroethyl)-4-phenyl-6-nitro-2(1H)-quinazolinone.

13. The compound according to claim 4 which is 1-(2,2,2-trifluoroethyl)-4-phenyl-6-trifluoromethyl-2(1H)-quinazolinone.

14. A pharmaceutical composition consisting essentially of an anti-inflammatorily and analgesically effective amount of a quinazolinone of claim 1 and pharmaceutically acceptable diluent or carrier.

* * * * *